(12) United States Patent
Witte et al.

(10) Patent No.: US 6,518,325 B2
(45) Date of Patent: Feb. 11, 2003

(54) HALOGEN-FREE, WATER-BLOWN, FLAME-RETARDANT RIGID POLYURETHANE FOAM AND A PROCESS FOR ITS PRODUCTION

(75) Inventors: Anne Witte, Greven (DE); Wilfried Krieger, Brühl (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/825,560

(22) Filed: Mar. 27, 2001

(65) Prior Publication Data

US 2001/0034377 A1 Oct. 25, 2001

(30) Foreign Application Priority Data

Mar. 27, 2000 (DE) .......................................... 100 14 596

(51) Int. Cl.$^7$ ............................................... C08G 18/14
(52) U.S. Cl. ...................... 521/169; 521/107; 521/108; 521/170; 521/174
(58) Field of Search ................................ 521/107, 108, 521/169, 170, 174

(56) References Cited

U.S. PATENT DOCUMENTS

| | | |
|---|---|---|
| 4,248,930 A | 2/1981 | Hass et al. |
| 4,263,408 A | 4/1981 | Meyborg et al. |
| 4,367,295 A | 1/1983 | von Bonin |
| 4,831,062 A | 5/1989 | von Bonin |
| 5,608,100 A | 3/1997 | Sicken |
| 5,776,992 A * | 7/1998 | Jung et al. .................. 521/107 |
| 5,985,965 A * | 11/1999 | Sicken et al. ............... 521/107 |

FOREIGN PATENT DOCUMENTS

| | | | |
|---|---|---|---|
| DE | 27 32 292 | | 2/1979 |
| DE | 28 32 253 | | 1/1980 |
| DE | 36 25 556 | | 2/1988 |
| DE | 3803030 | * | 8/1989 |
| DE | 43 42 972 | | 6/1995 |
| DE | 44 46 847 | | 7/1996 |
| DE | 19444426 | * | 7/1999 |
| DE | 197 44 426 | | 7/1999 |
| EP | 0 051 106 | | 5/1982 |
| EP | 0 632 046 | | 9/1995 |

OTHER PUBLICATIONS

German Office Action for DE 10014593.0,Jan. 16, 2001.
English Abstract for EP0051106, Jan. 4, 1983.
English Abstract for DE4446847, Jul. 3, 1996.
English Abstract for DE3625556, May 16, 1989.
English Abstract for DE19744426, Apr. 14, 1999.
Von W. Siefken, Justus Liebigs Annalen der Chemie, 562, pp. 76–136, (1948).
Carl Hanser Verlag, Kunststoff–Handbuch [Plastic Handbook], vol. VII, pp. 104 to 123, Munich, (1993).
EPO Search Report for Application No. 01106656, mail date Dec. 11, 2001.
Chemical Abstract XP002172650, Yanchuk, N. I., "Formation reaction of phosphorus–containing polyurethanes", (1981), 63, pp. 66–69.
English abstract XP002172651 for JP 52–027721, Mar. 2, 1977.
English abstract for EP 0632046, Sep. 4, 1995.
Copy of U.S. application, serial No. 09/818,417, filed Mar. 27, 2001.
Copy of U.S. application, serial No. 09/825,559, filed Mar. 27, 2001.

* cited by examiner

*Primary Examiner*—John M. Cooney, Jr.
(74) *Attorney, Agent, or Firm*—Anthony A. Bisulca

(57) ABSTRACT

The invention relates to a halogen-free, water-blown, flame-retardant rigid polyurethane foam, which comprises oxalkylated alkylphosphonic acids as flame retardant.

The invention further relates to a process for producing halogen-free, water-blown, flame-retardant rigid polyurethane foams, which comprises using oxalkylated alkylphosphonic acids as flame retardant.

Finally, the invention relates also to the use of oxalkylated alkylphosphonic acids of the formula I as halogen-free flame retardants for producing flame-retardant rigid polyurethane foams.

12 Claims, No Drawings

HALOGEN-FREE, WATER-BLOWN, FLAME-RETARDANT RIGID POLYURETHANE FOAM AND A PROCESS FOR ITS PRODUCTION

FIELD OF THE INVENTION

The invention relates to a halogen-free, water-blown, flame-retardant rigid polyurethane foam and to a process for its production, and also to the use of oxalkylated alkylphosphonic acids for producing rigid polyurethane foams of this type.

BACKGROUND OF THE INVENTION

Rigid polyurethane foams are used in many sectors, for example in the refrigeration industry, as insulating materials for construction, for example for heating units or composites, as packaging, and generally as industrial insulation. Rigid polyurethane foams generally have to be provided with flame retardants in order to achieve the high fire-protection requirements desirable in these sectors and sometimes required by legislation. A wide variety of different flame retardants is known and commercially available for this purpose. However, there are often considerable technical problems and toxicological concerns restricting the use of these flame retardants.

For example, when solid flame retardants such as melamine, ammonium polyphosphate or ammonium sulfate are used there are technical problems with metering which frequently necessitate complicated rebuilds or modifications of foaming plants.

Halogen-free flame retardant systems are preferred in principle for reasons of environmental toxicity, and also due to their better performance in terms of the smoke density and smoke toxicity associated with fires.

For flexible polyurethane foam systems, hydroxylated oligomeric phosphoric esters (DE-A-43 42 972) can be used as flame retardants. It is known that these compounds and their properties and effects cannot be similarly used in rigid polyurethane foam systems.

Although in principle flexible and rigid polyurethane foam systems may have approximately the same density and composition, flexible polyurethane foams have only slight crosslinking and exhibit only a low level of resistance to deformation under pressure.

In contrast, the structure of rigid polyurethane foams is composed of highly crosslinked units, and rigid polyurethane foam has very high resistance to deformation under pressure. A typical rigid polyurethane foam is of closed-cell type and has low thermal conductivity.

SUMMARY OF THE INVENTION

During the production of polyurethanes, which proceeds via the reaction of polyols with isocyanates, it is primarily the nature and chemistry of the polyol (functionality) which affects the subsequent foam structure and the properties of this material.

It is an object of the present invention to provide a halogen-free, water-blown, flame-retardant rigid polyurethane foam which does not have the abovementioned disadvantages and meets the necessary and prescribed requirements for flame retardancy, ease of production, low smoke density and low smoke toxicity.

The abovementioned object is achieved by means of a polyurethane foam of the type mentioned at the outset, which comprises oxalkylated alkylphosphonic acids as flame retardant.

DESCRIPTION OF THE PREFERRED EMBODIMENTS

The oxalkylated alkylphosphonic acids preferably have the formula I

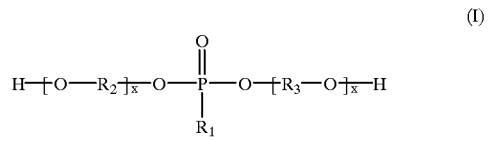

where
R$_1$ is a methyl, ethyl or propyl radical,
R$_2$ and R$_3$ are identical or different and are a methyl, ethyl or propyl radical and x is a number from 1.2 to 1.9.

It is preferable for R$_1$ to be a methyl radical, and x a number from 1.5 to 1.7. The value for x is the average chain length.

The halogen-free, water-blown, flame-retardant rigid polyurethane foam preferably comprises, based on the fully cured rigid polyurethane foam, from 0.1 to 30% by weight of the flame retardant.

The halogen-free, water-blown, flame-retardant rigid polyurethane foam particularly preferably comprises, based on the fully cured rigid polyurethane foam, from 5 to 20% by weight of the flame retardant.

The halogen-free, water-blown, flame-retardant rigid polyurethane foam preferably has a density of from 25 to 80 kg m$^3$.

It particularly preferably has a density of from 30 to 50 kg m$^3$.

The abovementioned object is also achieved by means of a process for producing halogen-free, water-blown, flame-retardant rigid polyurethane foams, which comprises using oxalkylated alkylphosphonic acids as flame retardant.

The oxalkylated alkylphosphonic acids preferably have the formula I

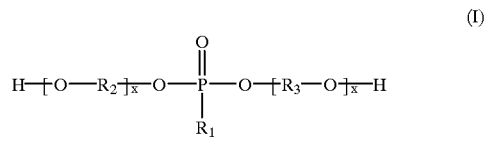

where
R$_1$ is a methyl, ethyl or propyl radical,
R$_2$ and R$_3$ are identical or different and are a methyl, ethyl or propyl radical and x is a number from 1.2 to 1.9.

The process is preferably executed by reacting organic polyisocyanates with compounds having at least two hydrogen atoms capable of reaction with isocyanates, with water as blowing agent, with stabilizers, with activators and/or with other conventional auxiliaries and additives, in the presence of oxalkylated alkylphosphonic acids of the formula I.

The oxalkylated alkylphosphonic acids of the formula I are preferably compounds liquid at processing temperature. For the purposes of the present invention, processing temperature is the temperature at which the starting components are mixed.

The oxalkylated alkylphosphonic acids of the formula I are preferably compounds reactive toward isocyanates.

The amount of the oxalkylated alkylphosphonic acids used of the formula I is preferably from 0.01 to 50 parts, based on 100 parts of polyol component.

The amount of the oxalkylated alkylphosphonic acids used of the formula I is particularly preferably from 10 to 35 parts, based on 100 parts of polyol component.

The invention also provides the use of oxalkylated alkylphosphonic acids of the formula I as halogen-free flame retardant for producing flame-retardant rigid polyurethane foams.

Regarding the rigid polyurethane foams:

These are mainly foams having urethane groups and/or isocyanurate groups and/or allophanate groups and/or uretdione groups and/or urea groups and/or carbodiimide groups. The use according to the invention preferably takes place during the production of polyurethane foams or of polyisocyanurate foams.

The materials used for producing the isocyanate-based foams are: Starting materials: aliphatic, cycloaliphatic, araliphatic, aromatic or heterocyclic polyisocyanates (see, for example, W. Siefken in Justus Liebigs Annalen der Chemie, 562, pp. 75–136), for example those of the formula $Q(NCO)_n$, where n=from 2 to 4, preferably from 2 to 3, and Q is an aliphatic hydrocarbon radical having from 2 to 18 carbon atoms, preferably from 6 to 10 carbon atoms, a cycloaliphatic hydrocarbon radical having from 4 to 15 carbon atoms, preferably from 5 to 10 carbon atoms, an aromatic hydrocarbon radical having from 6 to 15 carbon atoms, preferably from 6 to 13 carbon atoms, or an araliphatic hydrocarbon radical having from 8 to 15 carbon atoms, preferably from 8 to 13 carbon atoms, for example the polyisocyanates described in DE-A-28 32 253, pp. 10–11. Particular preference is generally given to the polyisocyanates readily available industrially and derived from tolylene 2,4- and/or 2,6-diisocayanate or from diphenylmethane 4,4'- and/or 2,4'-diisocyanate.

Other starting materials are compounds having at least two hydrogen atoms capable of reaction with isocyanates, with a molecular weight of from 400 to 10,000 ("polyol component"). For the purposes of the present invention, these are compounds having amino groups, thio groups or carboxyl groups, and preferably compounds having hydroxyl groups, in particular from 2 to 8 hydroxyl groups, and specifically those of molecular weight from 1000 to 6000, preferably from 2000 to 6000, and are generally polyethers or polyesters dihydric to octahydric, preferably dihydric to hexahydric, or else polycarbonates or polyesteramides, as known per se for the production of homogenous or of cellular polyurethanes, and as described in DE-A 28 32 253, for example. The at least dihydric polyethers and polyesters are preferred according to the invention.

Other starting materials which may be used if desired are compounds having at least two hydrogen atoms capable of reaction with isocyanates and with a molecular weight of from 32 to 399. In this case, again, for the purposes of the present invention these are compounds having hydroxyl groups and/or amino groups and/or thio groups and/or carboxyl groups, preferably compounds having hydroxyl groups and/or amino groups, and serving as chain extenders or crosslinkers. These compounds generally have from 2 to 8, preferably from 2 to 4, hydrogen atoms capable of reaction with isocyanates. Examples of these are again described in
DE-A-28 32 253.

If desired, concomitant use is made of auxiliaries and additions, such as catalysts of the type known per se, surface-active additives, such as emulsifiers and foam stabilizers, reaction inhibitors, e.g. substances of acid reaction, such as hydrochloric acid or organic acid halides, or else cell regulators of the type known per se, such as paraffins or fatty alcohols, and dimethylpolysiloxanes, or else pigments or dyes, or other flame retardants, or else stabilizers to counteract aging or weathering, core-discoloration inhibitors, plasticizers or fungistatic or bacteriostatic substances, or else fillers, such as barium sulfate, kieselgur, carbon black or whiting
(DE-A-27 32 292).

Pages 104 to 123 of Kunststoff-Handbuch [Plastics Handbook], Vol. VII, Carl Hanser Verlag, Munich, 1993 describe further examples of surface-active additives and foam stabilizers which may, if desired, be used concomitantly according to the invention, and also cell regulators, reaction inhibitors, stabilizers, flame-retardant substances, plasticizers, dyes and fillers, and also fungistatic or bacteriostatic substances, together with details of the manner of use of these additions, and of their manner of action.

Polyisocyanurate foams are produced using the processes and conditions known for this purpose.

EXAMPLES

The examples below illustrate the invention.

The following constituents were used for the experiments:

OMPA: Oxethylated methylphosphonic acid having a phosphorus content of 12.7% by weight, a hydroxyl value of 430 mg of KOH/g and a viscosity of 275 mPa s at 25° C.

OEPA: Oxethylated ethylphosphonic acid having a phosphorus content of 12.2% by weight, a hydroxyl value of 447 mg of KOH/g and a viscosity of 190 mPa s at 25° C.

OPPA: Oxethylated propylphosphonic acid having a phosphorus content of 12.3% by weight, a hydroxyl value of 421 mg of KOH/g and a viscosity of 160 mPa s at 25° C.

®Exolit OP550: A phosphoric polyester bearing hydroxyalkyl ester groups and having a phosphorus content of 17% by weight, a hydroxyl value of 130 mg of KOH/g and a viscosity of 2000 mPa s at 25° C.

(Manufacturer in each case: Clariant GmbH)

| | |
|---|---|
| Polyetherpolyol | ® Lupranol 3323, BASF, a polyether polyol having a hydroxyl value of 340 mg of KOH/g |
| Catalyts | N,N-Dimethylcyclohexylamine, Merck-Schuchardt |
| Stabilizer | ® Tegostab B8466, Th. Goldschmidt AG, a polyether-modified polysiloxane |
| Isocyanate | Caradate 30. ICI-Huntsman |

Examples 1 to 3

A water-blown rigid polyurethane foam (Index 130) with a density of about 40 kg/m³ was produced to the following mixing specification (data in parts by weight):

| Component | Example 1 | Example 2 | Example 3 (comparison) |
|---|---|---|---|
| Polyol Lupranol 3323 | 100.0 | 100.0 | 100.0 |
| Flame retardant | 25 | 30 | 100 |
| | OMPA | OEPA | Exolit OP550 |
| Catalyst DMCHA | 2.5 | 2.5 | 2.5 |

-continued

| Component | Example 1 | Example 2 | Example 3 (comparison) |
|---|---|---|---|
| Stabilizer Tegostab B 8466 | 3.0 | 3.0 | 3.0 |
| Blowing agent Water | 4 | 4 | 9 |
| Isocyanate Caradate 30 | Index 130 | Index 130 | Index 130 |

The rigid polyurethane foam was produced by mixing in the prescribed sequence, followed by foaming.

Fire Performance Testing

Fire performance is classified to DIN 4102 using the small burner test. If the requirements are complied with in the small burner test, the classification is B2. If the marking applied on the vertically arranged test sheet 150 mm above the point of flame application is reached by the upper boundaries of the flames within 15 seconds, the specimen tested is regarded as of high flammability, i.e. is allocated to building materials class B3.

Each of the abovementioned rigid polyurethane foams of the invention from Examples 1 and 2 passed the B2 test to DIN 4102. In addition, the result of measuring smoke density either under smoldering conditions or under flaming conditions was that this was reduced by a factor of from 3 to 10 in comparison with rigid polyurethane foams provided with halogen-containing flame retardants instead of the oxalkylated alkylphosphonic acids.

The product from Example 3 (comparison) did not pass the B2 test.

What is claimed is:

1. A halogen-free, water-blown, flame-retardant rigid polyurethane foam, which comprises oxalkylated alkylphosphonic acids as a flame retardant, and wherein the oxalkylated alkylphosphonic acids have the formula I

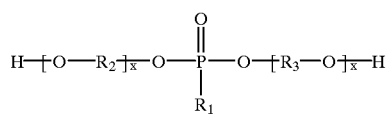

where
$R_1$ is a methyl, ethyl or propyl radical,
$R_2$ and $R_3$ are identical or different and are a methyl, ethyl or propyl radical and x is a number from 1.2 to 1.9.

2. The halogen-free, water-blown, flame-retardant rigid polyurethane foam as claimed in claim 1, wherein $R_1$ is a methyl radical and x is a number from 1.5 to 1.7.

3. The halogen-free, water-blown, flame-retardant rigid polyurethane foam as claimed in claim 1, which comprises, based on the fully cured rigid polyurethane foam, from 0.1 to 30% by weight of the flame retardant.

4. The halogen-free, flame-retardant rigid polyurethane foam as claimed in claim 1, which comprises, based on the fully cured rigid polyurethane foam, from 5 to 20% by weight of the flame retardant.

5. The halogen-free, flame-retardant rigid polyurethane foam as claimed in claim 1, which has a density of from 25 to 80 kg/m$^3$.

6. The halogen-free, flame-retardant rigid polyurethane foam as claimed in claim 1, which has a density of from 30 to 50 kg/m$^3$.

7. A process for producing halogen-free, water-blown, flame-retardant rigid polyurethane foams which comprises using oxalkylated alkylphosphonic acids as a flame retardant, and wherein the oxalkylated alkylphosphonic acids have the formula I

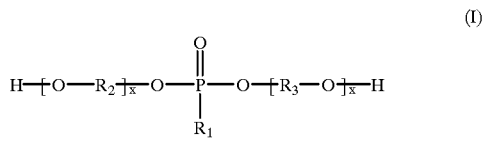

where
$R_1$ is a methyl, ethyl or propyl radical,
$R_2$ and $R_3$ are identical or different and are a methyl, ethyl or propyl radical and x is a number from 1.2 to 1.9.

8. The process as claimed in claim 7, wherein organic polyisocyanates are reacted with compounds having at least two hydrogen atoms capable of reaction with isocyanates, with water as blowing agent, with stabilizers, with activators and/or with other auxiliaries and additives, in the presence of oxalkylated alkylphosphonic acids of the formula I.

9. The process as claimed in claim 7, wherein the oxalkylated alkylphosphonic acids of the formula I are compounds liquid at processing temperature.

10. The process as claimed in claim 7, wherein the oxalkylated alkylphosphonic acids of the formula I are compounds reactive toward isocyanates.

11. The process as claimed in claim 7, wherein, based on 100 parts of polyol component, the amount used of the oxalkylated alkylphosphonic acids of the formula I is from 0.01 to 50 parts.

12. The process as claimed in claim 7, wherein, based on 100 parts of polyol component, the amount used of the oxalkylated alkylphosphonic acids of the formula I is from 10 to 35 parts.

* * * * *